United States Patent
Richman (10) Patent No.: US 12,036,050 B1
(45) Date of Patent: Jul. 16, 2024

(54) MANAGEMENT SYSTEMS FOR SURGICAL INSTRUMENTS AND ITEMS USED DURING SURGERY

(71) Applicant: Sure Count Surgical, LLC, Los Angeles, CA (US)

(72) Inventor: Lawrence M. Richman, Los Angeles, CA (US)

(73) Assignee: Sure Count Surgical, LLC, Los Angeles, CA (US)

( * ) Notice: Subject to any disclaimer, the term of this patent is extended or adjusted under 35 U.S.C. 154(b) by 0 days.

(21) Appl. No.: 18/140,505

(22) Filed: Apr. 27, 2023

(51) Int. Cl.
*A61B 50/33* (2016.01)
*A61B 90/00* (2016.01)

(52) U.S. Cl.
CPC ...... *A61B 50/33* (2016.02); *A61B 2090/0804* (2016.02); *A61B 2090/0807* (2016.02)

(58) Field of Classification Search
CPC ......... A61B 50/30; A61B 50/22; A61B 50/20; A61B 50/34; A61B 50/33
USPC .......... 206/370, 363, 53, 451; 248/542, 689, 248/675, 27.3, 534, 540, 74.1, 201, 248/223.41
See application file for complete search history.

(56) References Cited

U.S. PATENT DOCUMENTS

| | | | |
|---|---|---|---|
| 3,132,765 A | 5/1964 | Florendo | |
| 3,983,996 A | 10/1976 | Hendren, III | |
| 3,987,895 A | 10/1976 | Jamshidi | |
| 4,011,944 A | 3/1977 | Cooley et al. | |
| 4,046,254 A | 9/1977 | Kramer | |
| 4,153,160 A | 5/1979 | Leigh | |
| 4,767,008 A | 8/1988 | Metz | |
| 5,170,804 A | 12/1992 | Glassman | |
| 5,294,413 A | 3/1994 | Riihimaki et al. | |
| 5,441,152 A | 8/1995 | Estes | |
| 5,505,916 A | 4/1996 | Berry, Jr. | |
| 6,230,888 B1 | 5/2001 | Amster | |
| 6,426,041 B1 | 7/2002 | Smith | |
| 7,066,328 B2 | 6/2006 | Pulsifer | |
| 7,997,847 B2 | 8/2011 | Treat et al. | |
| 8,177,064 B2 | 5/2012 | McCormick et al. | |

(Continued)

FOREIGN PATENT DOCUMENTS

| | | |
|---|---|---|
| AU | 2015328645 | 4/2017 |
| CA | 2963513 A1 | 4/2016 |

(Continued)

OTHER PUBLICATIONS

Amiwelisten, "Surgical Instrument counting and organizational system," YouTube, Feb. 14, 2008 https://www.youtube.com/watch?v=Oyb7i7WafAo.

(Continued)

*Primary Examiner* — Robert Poon
(74) *Attorney, Agent, or Firm* — Michael D. Harris; Angelo J. Gaz; SoCal IP Law Group LLP (57) ABSTRACT

The management system mounts rear upright instrument supports on the base of a tray. Each rear support holds the rear end of surgical instruments such as forceps or scissors with the finger holes spaced apart. The forward end of the instruments are held by a forward support. That support has a bar over the instruments, which is positioned to be horizontal when the forward support (and the rear support) is full.

4 Claims, 9 Drawing Sheets

(56) References Cited

U.S. PATENT DOCUMENTS

| | | | | |
|---|---|---|---|---|
| 8,240,473 | B2* | 8/2012 | Van Patten | B65D 81/107 |
| | | | | 206/451 |
| 8,627,987 | B2 | 1/2014 | Pollack et al. | |
| 9,179,978 | B1 | 11/2015 | Richman | |
| 9,474,579 | B2 | 10/2016 | Richman | |
| 2004/0182973 | A1* | 9/2004 | Kawai | H02G 3/32 |
| | | | | 248/74.1 |
| 2004/0206711 | A1 | 10/2004 | Hoftman | |
| 2006/0175209 | A1 | 8/2006 | Sabilla et al. | |
| 2006/0266666 | A1 | 11/2006 | Bettenhausen et al. | |
| 2007/0023305 | A1 | 2/2007 | Chan et al. | |
| 2007/0095717 | A1 | 5/2007 | Tucker | |
| 2007/0205123 | A1* | 9/2007 | Bettenhausen | A61B 50/34 |
| | | | | 206/370 |
| 2007/0215757 | A1* | 9/2007 | Yuta | F16L 55/035 |
| | | | | 248/68.1 |
| 2008/0149807 | A1* | 6/2008 | Chen | F04D 29/601 |
| | | | | 248/675 |
| 2009/0266728 | A1* | 10/2009 | Turner | A61B 17/865 |
| | | | | 206/459.1 |
| 2010/0065456 | A1 | 3/2010 | Junk et al. | |
| 2010/0148015 | A1* | 6/2010 | Matsuno | F16L 3/1075 |
| | | | | 248/65 |
| 2011/0114522 | A1 | 5/2011 | Alston et al. | |
| 2012/0217354 | A1* | 8/2012 | Walraven | F16L 3/1091 |
| | | | | 248/74.1 |
| 2012/0318935 | A1* | 12/2012 | Benedetti | F16L 3/227 |
| | | | | 24/457 |
| 2014/0083886 | A1 | 3/2014 | Winterrowd et al. | |
| 2014/0166825 | A1* | 6/2014 | Shiga | H02G 3/32 |
| | | | | 248/74.2 |
| 2018/0256766 | A1* | 9/2018 | Gareiss | F16B 2/22 |
| 2019/0255207 | A1* | 8/2019 | Oko | A61L 2/07 |
| 2021/0338357 | A1* | 11/2021 | Lenzenhuber | A61B 50/30 |
| 2022/0338872 | A1* | 10/2022 | Kelly | A61B 17/06114 |
| 2023/0218361 | A1* | 7/2023 | Pfefferle | A61B 50/33 |
| | | | | 206/438 |

FOREIGN PATENT DOCUMENTS

| | | |
|---|---|---|
| CN | 201949149 U | 8/2011 |
| CN | 203089415 U | 7/2013 |
| CN | 203524844 U | 4/2014 |
| CN | 106999253 A | 8/2017 |
| DE | 20318732 U1 | 2/2004 |
| EP | 3203923 A1 | 8/2017 |
| HK | 1240803 B | 6/2018 |
| IN | 201737013511 A | 8/2017 |
| JP | 2002102252 A | 4/2002 |
| JP | 2017534371 A | 11/2017 |
| KR | 20170065550 A | 6/2017 |
| RU | 2017113522 A | 11/2018 |
| WO | 2016057102 A1 | 4/2016 |

OTHER PUBLICATIONS

Utah Medical Products, Inc. "Developmentally Friendly-Neonatal and Pediatric Intensive Care," http://www.utahmed.com/pdf/58105.pdf, Jun. 30, 2013pp. 1-14.
Utah Medical Products, Inc. "Umbili-Cath," http://web.archive.org/web/20130630061754/http://www.utahmed.com/umbilicath.htm, Jun. 30, 2013pp. 1-4.
World Intellectual Property Organization, International Search Report and Written Opinion for International Application No. PCT/US2015/42307, mail date Oct. 29, 2015pp. 1-14.
European Patent Office, Extended European Search Report for Application No. EP15848431, date Mar. 28, 2018, pp. 1-7. 2018.
Protrusion of Plastic, Photograph, Creator Unknown, 1 page.
White Double Tray Basket, Photograph, Creator Unknown, 1 page.
Surgical Instrument Tray with Two Layers, Brown, Photograph, Creator Unknown, 1 page.
Surgical Instrument Tray with Two Layers, Metal, Photograph, Creator Unknown, 1 page.
Double Layer Sterilization Tray with Silicone Pad Disinfection Box Surgical Autoclavable Surgery, AliExpress.com, 1 page.
Mesh Baskets, Photographs, Creator Unknown, 3 pages.
Video "Innovative, Custom Sterilization Container Systems," Jewel Precision, https://jewelprecision.com/#.
Surgical Instrument Tray for Multiple Instruments Vertical Blue, Photograph, Creator Unknown, 1 page.
Surgical Instrument Tray for Multiple Instruments Vertical, Photograph, Creator Unknown, 1 page.

* cited by examiner

MANAGEMENT SYSTEMS FOR SURGICAL INSTRUMENTS AND ITEMS USED DURING SURGERY

BACKGROUND

1. Field: Management systems for surgical instruments in operating rooms.

2. General Background and State of the Art: Surgeons and their staff need their instruments and other items used during surgery to be readily accessible and well organized. Looking for forceps hidden by or contacting other instruments, for example, adds crucial time to a surgery. That is undesirable for the patient because delays increase the length of the surgery and excessive time under anesthesia, and it increases the risk of post-operative infection.

Increasing the time for each surgery also is detrimental to surgeons, other physicians, and staff and to the hospital or surgical center. Delays for each surgical team compound the delays for other teams, which also can delay the next procedure and limit operating room efficiency and increased patient pass through.

After each surgery, the team commonly takes all surgical instruments used during surgery or taken into the operating room and mounts them through their finger openings on a stringer, two parallel, spaced stainless steel rods. The rods (stringers) organize and hold the instruments together for easier transport and organization but fall short of individual instrument identification and ready access. The instruments are sprayed with a disinfectant that kills microbes that might otherwise float freely into the hospital corridors during transport back to the sterilization processing department as well as becoming airborne within the sterilization department itself. Loading the instruments on the rods, removing them for sterilization and then organizing them for another surgery are time-consuming, inefficient activities that increases the risk of glove punctures or dropping instruments to the floor requiring replacements.

Increased costs and decreased efficiency are not the only concerns. Each team must account for all instruments when the procedure starts and ends. As an illustration, if the team starts with a ten of one instrument and uses all but three, they must account for the seven used and the three unused. If any are missing, the team must determine how many instruments are missing. Once known, locating one or more missing instruments may be difficult and time consuming, all of which adds up to the duration of the procedure especially when accounting for each surgery, each operating room, each hospital, and hospitals in general. Some estimates assume $40/minute for each operating room delay.

The managed instruments must be sterile for use during surgery, and particular attention must be directed to observing instruments from coming in contact with non-sterile areas or objects in the operating room. This management system facilitates sterilization of instruments, organizes them together and diminishes inadvertent contamination in the operating room. Doing so is more efficient than sterilizing the instruments separately and then loading the instruments for each upcoming surgery.

High-temperature steam used to sterilize instruments could adversely affect management systems' components, so choosing the parts of the system that the heat and substances will not damage is important.

Different surgical procedures, e.g., cardiac versus orthopedic, often require different instruments and different amounts of the same instrument. The management system greatly facilitates organization, accountability, and chain of custody of the surgical instruments.

SUMMARY

The management system for holding surgical instruments includes a tray having a base. The tray may have sidewalls and a cover extending to the sidewalls over the base. The base has openings to let the steam and EO gas circulate around the surgical instruments. The sidewalls and cover may have similar openings.

Rear upright instrument supports attach to the base, and each support holds the handle end of a stack of surgical instruments. The rear upright instrument supports have projections that conform to structures of one end of the surgical instruments. The rear upright instrument support has at least one foot, each of which attaches to the base.

A forward support, which also is secured to the tray's base, is positioned forward of the rear upright instrument support and its stack of surgical instruments. The forward supports hold the forward part of the instruments. For many instruments, the forward support is near the instrument's hinge, but it may be spaced from the hinge, especially for longer forceps or other instruments. The forward support has space-apart members that may be U-shaped, and each space-apart member has spaced apart segments. A single member may replace the two, spaced-apart members. The other ends of the instruments rest between the forward support's members. An arm mounts on a hinge between the segments of one space-apart member and extends toward the segments of the other space-apart member. When the stack of instruments has a predetermined number of instruments, the arm contacts the top instrument and is horizontal, i.e., parallel with the tray's base.

The arm pivots upward to load the instruments and to be free of the instruments so the upper most instrument of the stack of instrument can be added or removed from the stack. Each time the top instrument is removed from the stack, the arm pivots back below the horizontal starting position to rest on what becomes the top instrument. When another instrument is removed from the stack, the arm can pivot farther.

Numbers may be printed on the forward support near the end of the arm. The number "1" is positioned where the end of the arm drops when one instrument is removed from the forward support. "2" is positioned where the end of the arm is when the second instrument is removed, and so on. The numbers would alert the operative team what instruments are in use in real time, what instrument(s) may be missing deep within a body cavity or under a drape, floor, etc. The security alert bar is restricted from descending too far out of finger reach by a horizontal metal bar between the two sidewalls.

The type of instrument can be printed on the base or on the supports.

DETAILED DESCRIPTION

Figure 2:
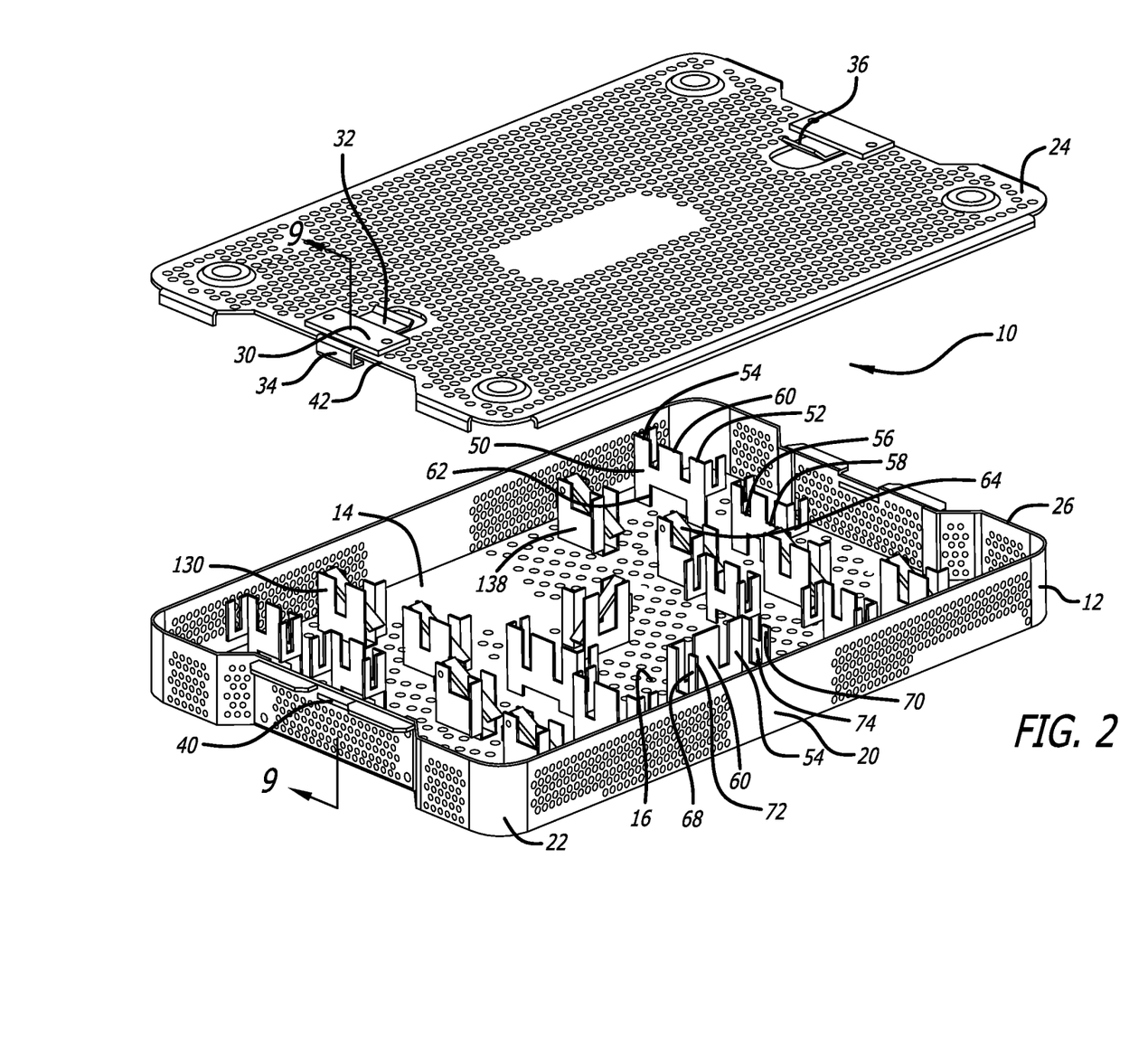
FIG. 2 is a perspective view of the management system with a top cover released and elevate so the internal structure is visible.
Figure 3:
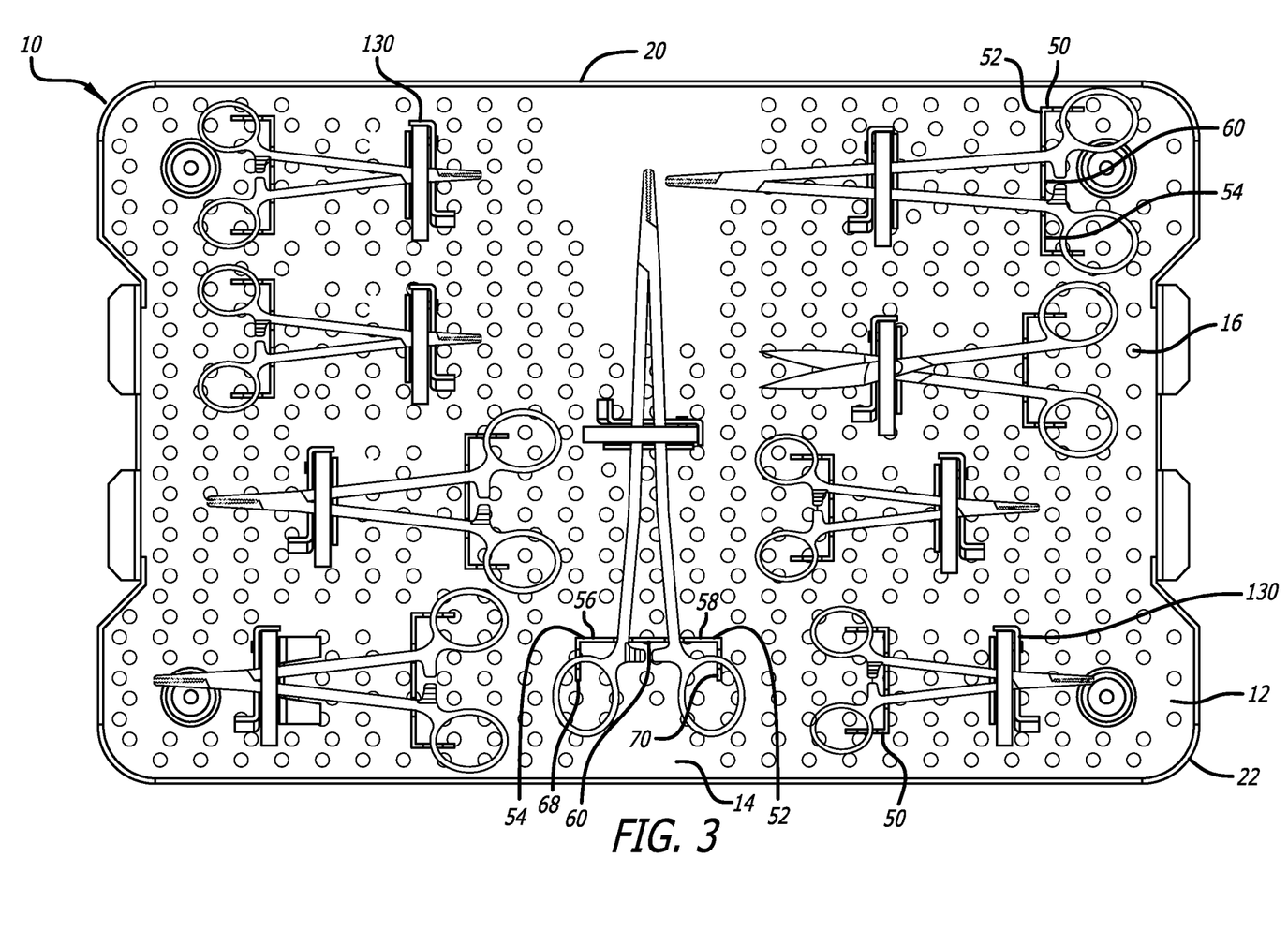
FIG. 3 is a plan view of the management system.

Management system 10 includes a tray 12 with a base 14 (FIGS. 2, 3). The tray has an array of openings 16, which are circular and aligned in FIGS. 2 and 3, but the openings may be other shapes, and may be arranged differently.

Figure 1:
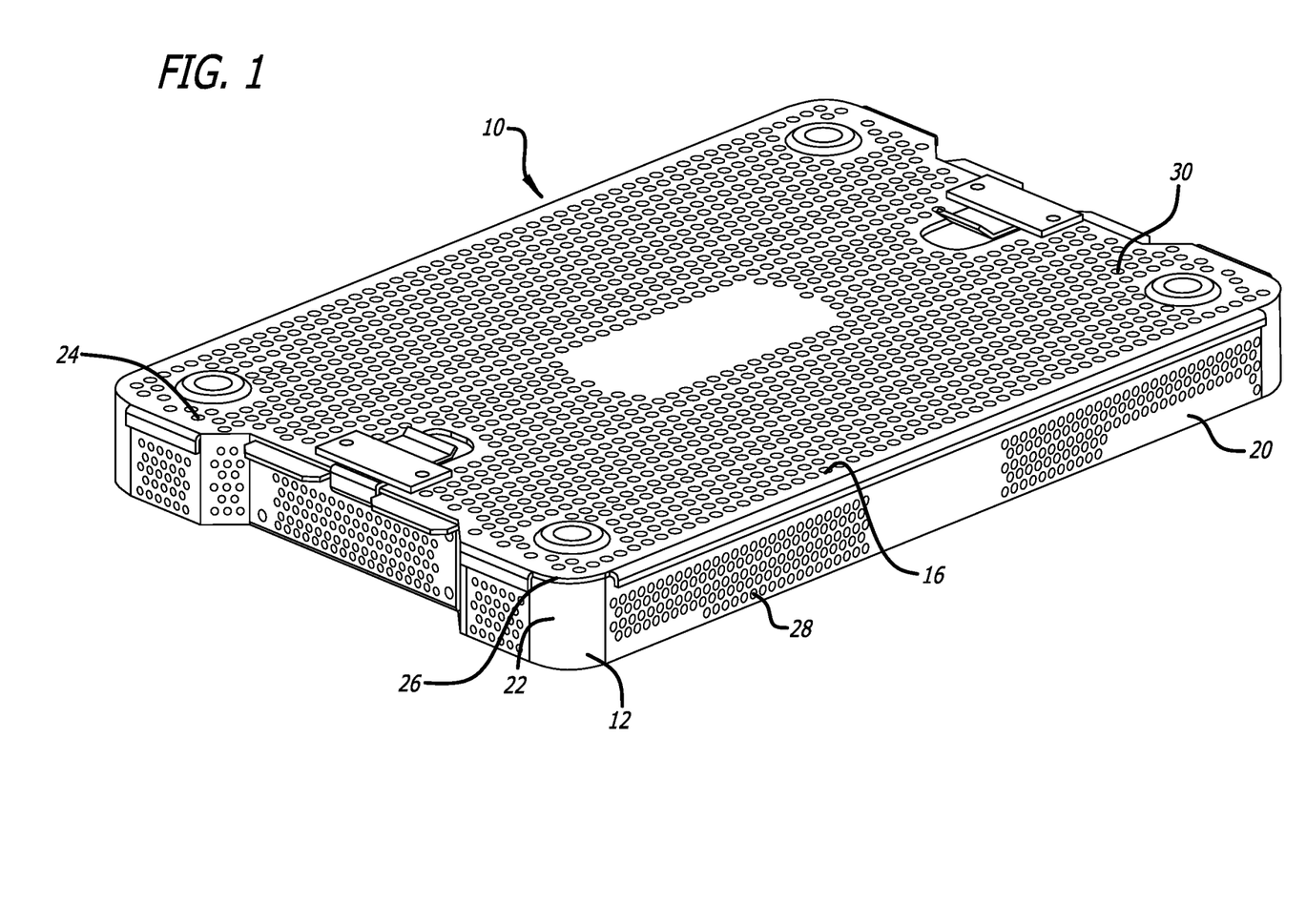
FIG. 1 is a perspective view of the management system with an attached top cover.

Sidewall 20 extends upright from the four side edges of base 14. The corners 22 of the sidewalls may be curved to avoid sharp corner edges. The sidewall also has an array of openings 28, which may be of a different size or shape from openings 16 in the base. Lid 24 (FIG. 1) may attach to the top 26 of the sidewall. The lid also has an array of openings 30.

Base 14 or other parts may have printing showing the instrument for each location.

Figure 9:
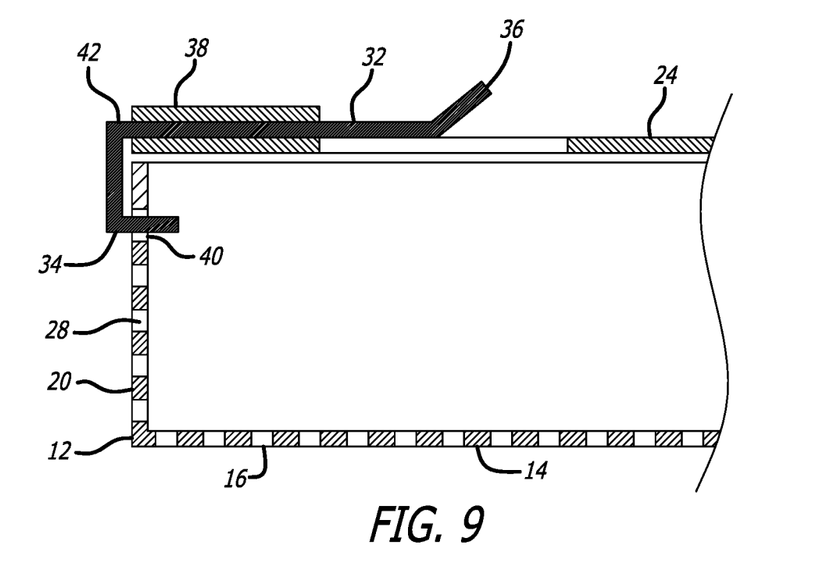
FIGS. 9 and 10 are sectional views through plane 9-9 of FIG. 2 showing the system's locking mechanism.
Figure 10:
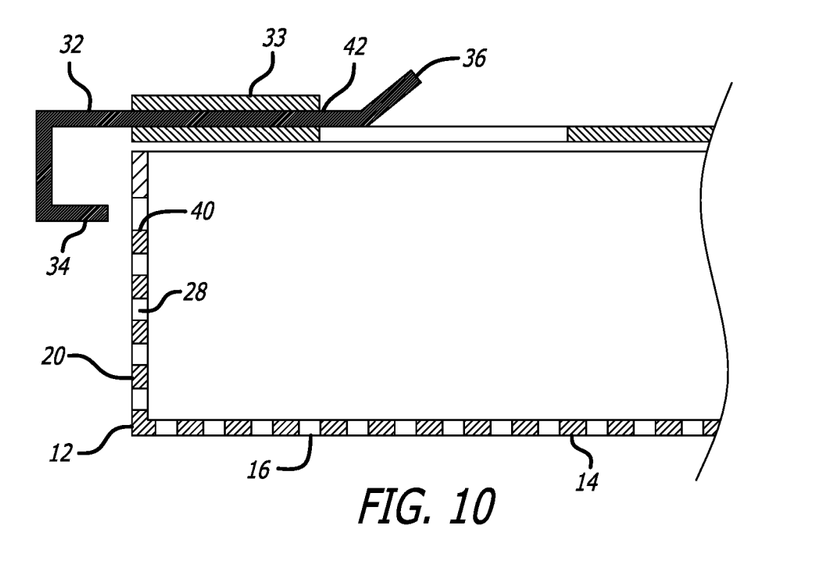

Lid 24 can be secured to tray 12. See FIGS. 1, 9, and 10. Slider 32 can move horizontally in opening 42. The slider may have a finger-gripping projection 36 and an engagement projection 34. Pulling on the slider to the right (FIGS. 9 and 10) moves the engagement projection in slot 40. Pushing the slider to the left moves the engagement projection out of the slot to release lid 24.

The tray's dimensions may vary. In one system, tray 12 may be 51.5 mm wide and 32.5 mm deep. Sidewall 20 may be 4.8 mm high. With lid 24 attached to the tray, the overall dimensions of the tray are 52.5 mm wide, 33.5 mm deep, and 5 mm high. The tray can fit within a wide-body Aesculap® SterilContainer. See www.aes-culapusa.com (accessed Mar. 29, 2023). Steam and EO pass through openings 16, 28, and 30 and reach the instruments in the tray to sterilize them. The base, sidewall, and lid may be aluminum, but they may be other non-corrosive materials that the heat and chemicals do not affect adversely during sterilization. Depending on the height of the tray including its sidewall, mounting two trays together, one above another, may fit in Aesculap containers. Other manufacturers may expand the width of their sterilization containers to accommodate the present management system. If wider modules are not in stock, standard hospital procedure allows wrapping any item in CSR wrap, sterilizing the contents in the wrap, and sending it to the operating room. Depending on the instruments loaded on the tray, a fully laden tray weighs about 2¾ kg (≈6 lbs.).

Rear upright instrument support 50 attach to base 14 for holding instruments in tray 12. See FIGS. 2, 3 and 8. See also rear upright instrument support 80 (FIG. 6) and rear upright instrument support 100 (FIG. 7). Support 50 may be stamped stainless steel or another non-corrosive material. The rear upright instrument supports may be attached to the base using automatic laser welding or other fastening techniques. Openings (not shown) may be provided in the base into which structure from the rear upright instrument supports extends for fastening.

Rear upright instrument supports can have different configuration that may depend on the instruments they hold. Because of the number of rear upright instrument supports in FIGS. 2 and 3 and the distances between them, reference numbers may be on the elements of different supports. But FIG. 8 shows one rear upright instrument support with elements spaced far enough apart.

Rear upright instrument support 50 (FIGS. 2 and 3-FIG. 3 also shows instruments) has first and second, spaced apart standing members 52 and 54 with at least one gap between the standing members. The rear upright instrument support in FIGS. 1 and 2 have two gaps 56 and 58 with center plate 60 between the gaps. The bottom of legs 62 and 64 contact the surface of base 14. The bottoms may be automatically laser welded to base 14 though the system can use other modes of fastening. The drawings do not show the structure at the bottom of the legs for attaching the legs to base 14.

In FIG. 2, each rear upright instrument support has rear-facing panels 68 and 70. Each panel has a groove 72, 74.

Figure 8:
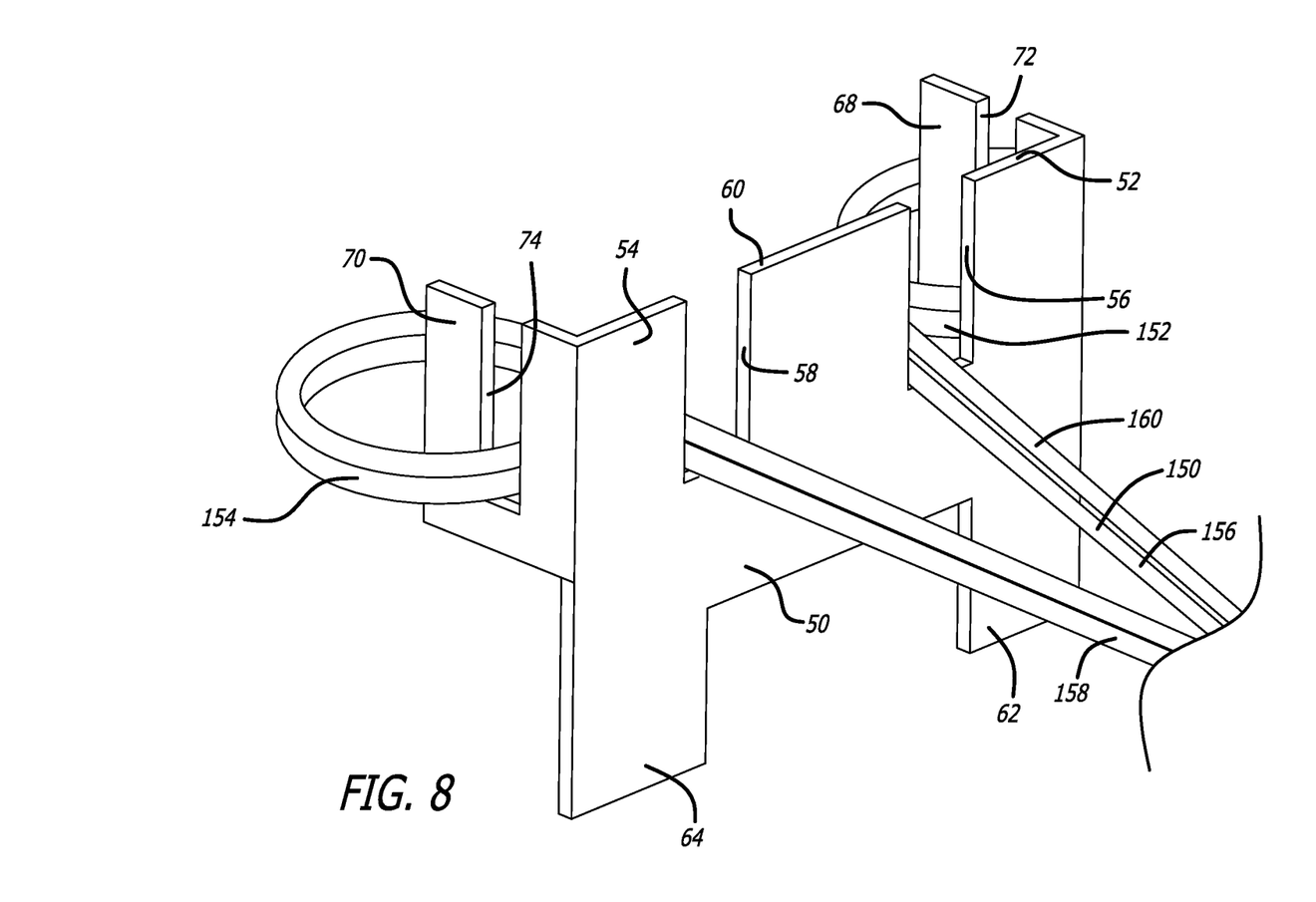
FIG. 8 is a perspective view of another version of the management system's rear upright instrument support holding part of the handles of an instrument.

FIG. 8 shows how the described rear upright instrument support 50 holds the handle ends of instrument such as forceps 150. The structure around finger holes 152 and 154 of the bottom forceps rests at the bottom of grooves 72 and 74, and shanks 156 and 158 rest of the bottom of gaps 56 and 58. Forceps 160 is above forceps 150, and the depths of the gaps and grooves allow for additional instruments. The structure holds the instruments securely so that they project forward from the support without moving much left to right.

The rear upright instrument supports may position the instruments they hold with the jaws of forceps or the blades of scissors apart (see FIG. 3) for sterilization of the jaws or blades.

Figure 6:
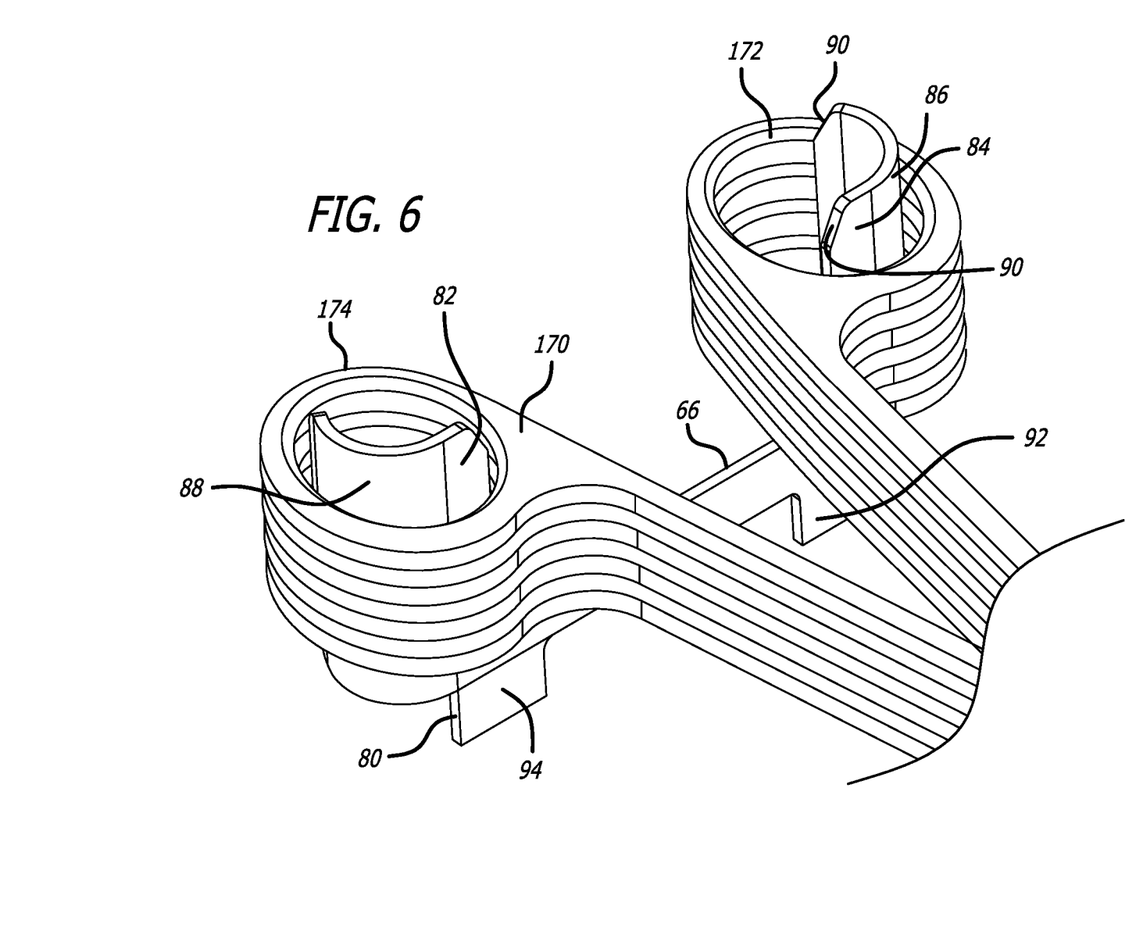
FIG. 6 is a perspective view of one version of the management system's rear upright instrument support holding part of the handles of an instrument.
Figure 7:
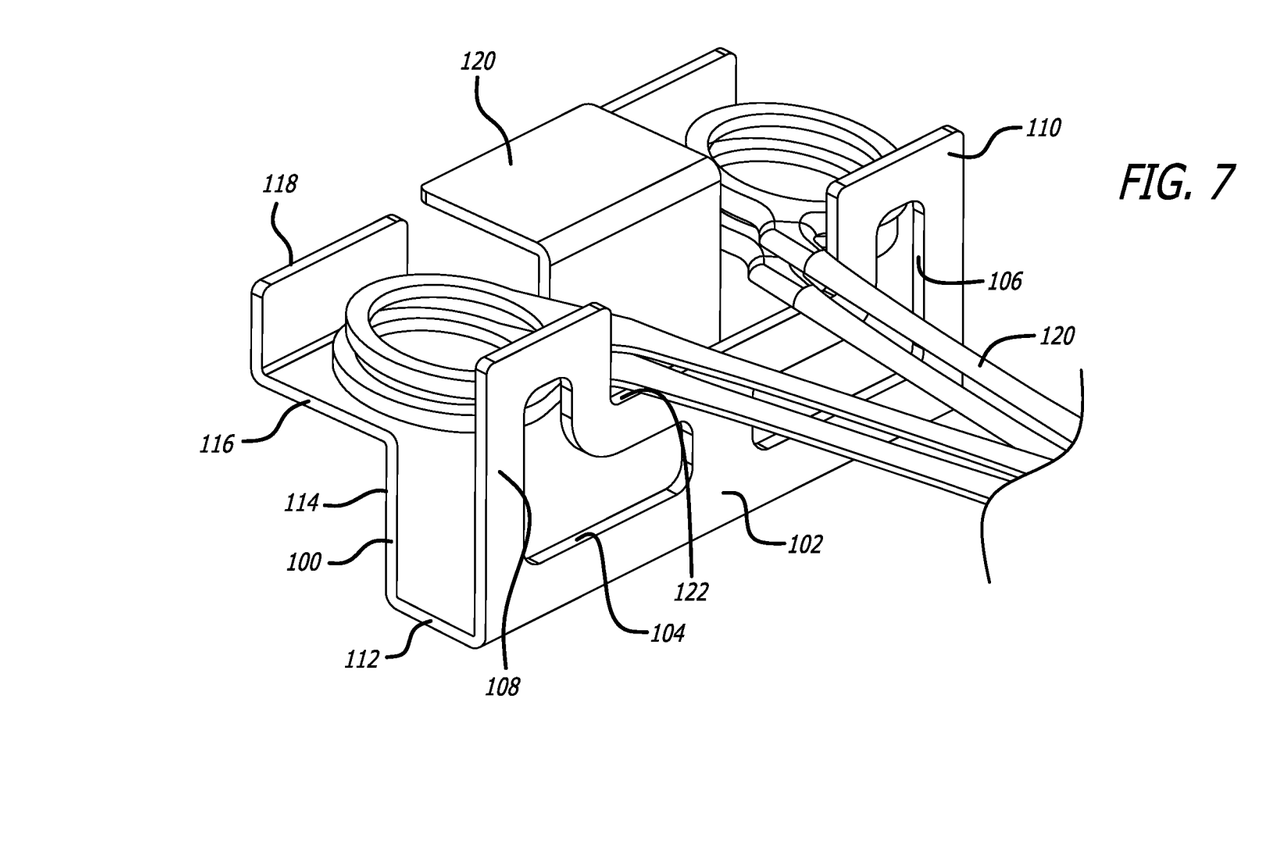
FIG. 7 is a perspective view of another version of the management system's rear upright instrument support holding part of the handles of an instrument.

FIG. 6 shows a different rear upright instrument support 80 for holding the handle end of an instrument such as forceps 170. Spaced-apart standing members 82 and 84 extend into curved sections 86 and 88. The structure around finger holes 172 and 174 may conform to the curved sections. The curved section may have offset ends to help placing the instrument's finger openings on the curved section.

Legs 92 and 94 of rear upright instrument support 80 are shorter than the legs of support 50 (FIG. 8). Support 80 holds more instruments so the shorter legs position the top instrument at about the same height for both supports.

Standing members 82 and 84 have no center plate like plate 60 in FIG. 8. Thus, gap 66 in FIG. 6 is uninterrupted and wider.

FIG. 7 shows a third rear upright instrument support 100. It may be formed from bent sheet stainless steel. It has a front, upright wall 102 with two cutouts 104 and 106 and two upright extensions 108 and 110, which extend from base 112. Rear wall 114 extends upward from the base, and it bends rearward at 116 and then upward to 118 to form a shelf for the rear end of forceps. Spacer 120 keeps the rear of the forceps apart. The spacer and the inside of upright extensions 108 and 110 secure the rear of the forceps. Ledge 122 is a support surface of the bottom-most instrument.

When the management system is set to have a particular number of instruments, the rear upright instrument supports can be chosen to have corresponding distances for the instrument support surfaces above base 14. From that height, the distance of the top instrument can be determined. If the distance of all top instruments above the base is the same, the system can use rear upright instrument supports with the correct distance from the base to the surface supporting the bottom instrument.

Forward supports 130 (FIGS. 2-5) mount forward of each rear upright instrument support. For many forceps or scissors, the forward supports are positioned at or near where the hinge will be when the instruments mount in the rear upright instrument supports.

Figure 4:
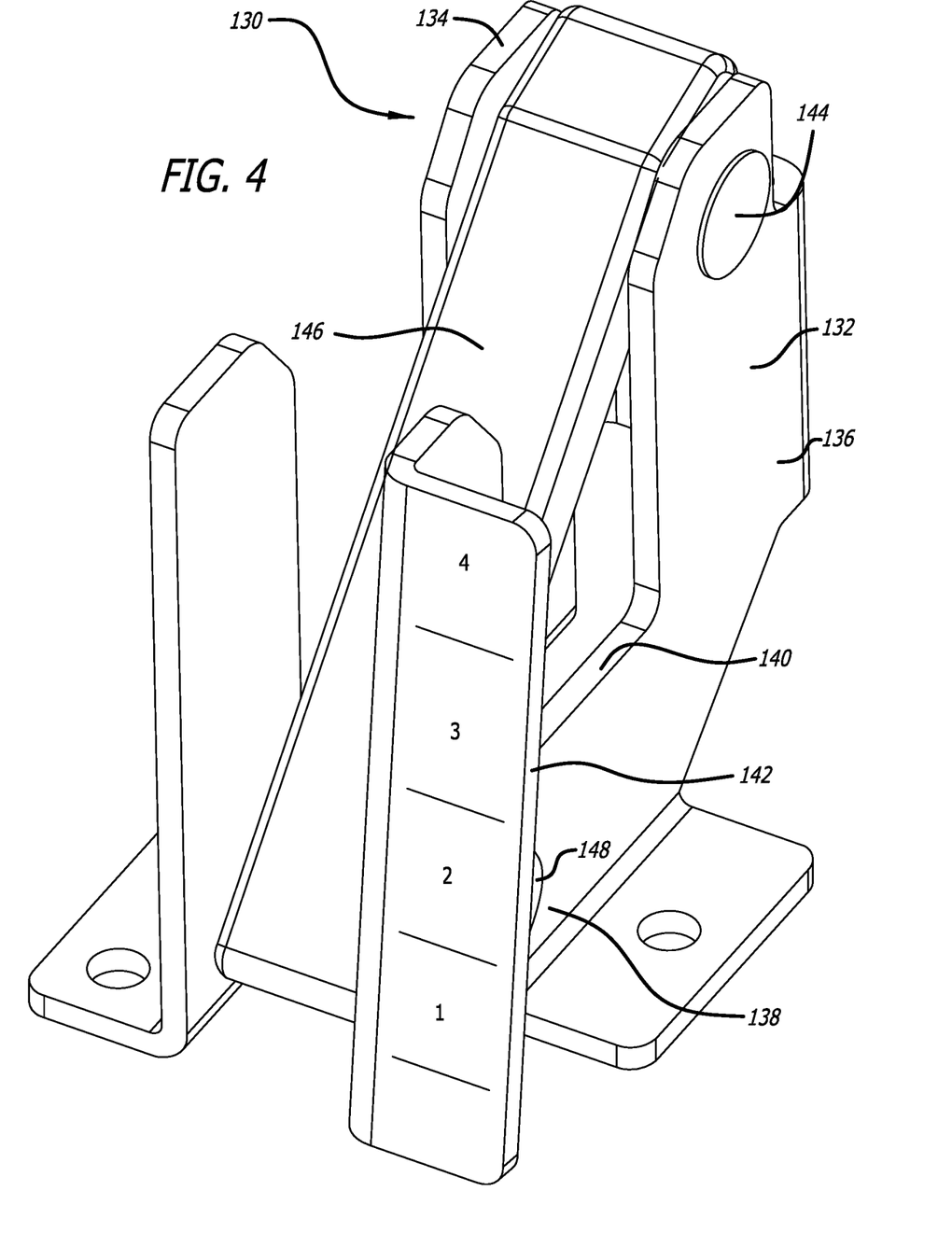
FIG. 4 is a perspective view of a forward support for the management system.
Figure 5:
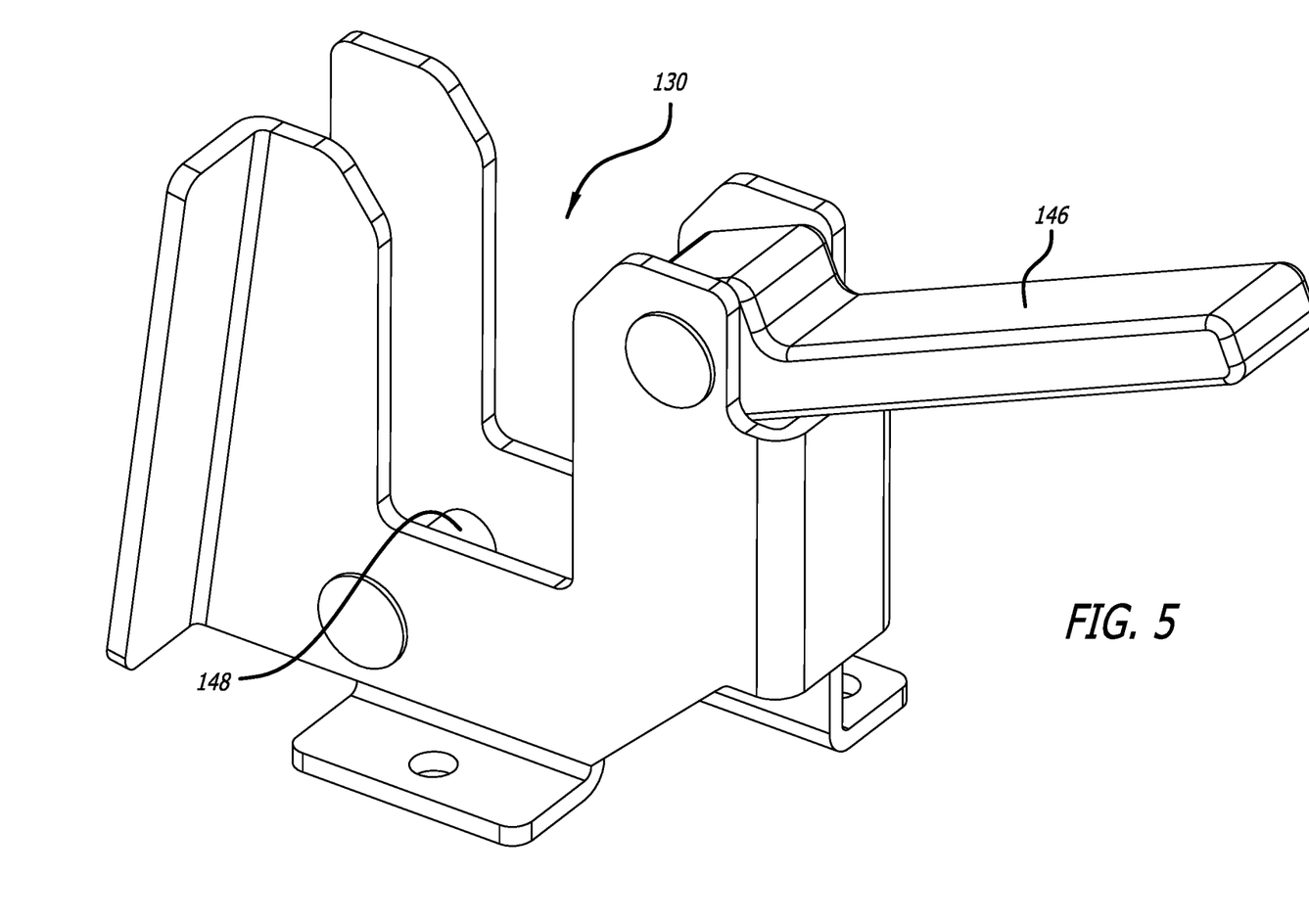
FIG. 5 is another perspective view of a forward support for the management system with an arm in an open position.

Forward support 130 in FIGS. 4 and 5 has first and second spaced-apart members 132 and 134. Having two members spaced apart adds rigidity to the forward support, but a single member could be acceptable. Upright member 132 has first and second sides 136 and 138 with platform 140 between the sides. The platform is the surface on which the bottom surgical instrument rests.

When a second member 134 is used, it has a shape like the shape of first member 132. Both members are welded to base 14.

Gauge 142 extends upward for the second side of the first member. Pin or hinge 144 mounts through the first side of the platform, and the proximal end of bar 146 mounts for pivoting on the hinge. The bar's distal end extends near the gauge. The gauge is designed so that bar 146 will be horizontal and aligned with the "4" on the gauge when the system holds four instruments. If four instruments are removed, the bar drops below the "1" and contacts stop 148.

Bar 146 can pivot to and beyond vertical, see FIG. 5, to remove instruments and to return them to forward supports 130. During surgery, the bar should not remain in the FIG. 5 position. If an instrument is removed, the bar should be pivoted back-counter-clockwise in FIG. 5. If instruments are being reloaded after surgery, the bar can remain in the FIG. 5 position until the forward support is full. If the bar is above horizontal after it is fully loaded, it indicates that the support is overloaded.

The description is illustrative, not limiting and is for example only. Although this application shows and describes examples, those having ordinary skill in the art will find it apparent they can make changes, changes, or alterations. Many examples involve specific combinations of method acts or system elements, but those acts and those elements may be combined in other ways to meet the same goals. Acts, elements, and features discussed only with one embodiment are not intended to be excluded from a similar role in other embodiments.

"Plurality" means two or more. A "set" of items may include one or more of such items. The terms "comprising," "including," "carrying," "having," "containing," "involving," and similar words in the written description or the claims are open-ended, i.e., each means, "including but not limited to." Only the transitional phrases "consisting of" and "consisting essentially of" are closed or semi-closed transitional phrases regarding claims. The ordinal terms like "first," "second," "third," etc., in the claims don't by themselves connote any priority, precedence, or order of one claim element over another or the temporal order in which acts of a method are performed. Instead, they merely are labels to distinguish one claim element having a certain name from another element having a same name (but for the ordinal term's use). Alternatives like "or" include one or any combination of the listed items.

I claim:

1. A management system for holding surgical instruments of which the surgical instruments include a handle part and a part forward of the handle part, the management system comprising:
   a tray having a base,
   a rear upright instrument support mounted on the base and a forward upright instrument support mounted on the base spaced from the rear upright instrument support,
   the rear upright instrument support configured for holding the handle part of a plurality of surgical instruments in an aligned stack from a bottommost instrument to a topmost instrument in which each handle part of the aligned stack of instruments is in contact with the handle part of the adjacent instruments, each instrument being in a generally fixed position,
   the forward upright instrument support having a first platform positioned to support the part forward of the handle part of each surgical instrument in an aligned stack,
   wherein the forward support comprises first and second spaced apart upright members attached to the base, each upright member having first and second sides and a second platform between the first and second sides on which part of a surgical instrument can contact,
   the management system further comprising a hinge extending from the first side of the first spaced apart upright member and the first side of the second spaced apart upright member, and a bar having a first end pivotally mounted on the hinge and positioned to contact the topmost instrument, the bar having a distal end spaced from the first end, and the bar being adapted to pivot between a first position in contact with the topmost surgical instrument to a second position in which fewer surgical instruments are in the stack of surgical instruments when a part of a surgical instrument is removed from the forward support.

2. The management system of claim 1, further comprising a stop extending between the first spaced apart upright member and the second spaced apart upright member in a path of the bar.

3. The management system of claim 1, the management system further comprising a gauge positioned near the distal end of the bar.

4. The management system of claim 1, wherein the forward support is positioned at or near where the hinge will be when the instruments are in the rear upright instrument supports.

* * * * *